(12) United States Patent
Asgharian

(10) Patent No.: US 6,495,608 B1
(45) Date of Patent: Dec. 17, 2002

(54) METHODS OF PERFORMING SURGERY WITH GALACTOMANNAN POLYMERS AND BORATE

(75) Inventor: Bahram Asgharian, Arlington, TX (US)

(73) Assignee: Alcon Manufacturing, Ltd., Fort Worth, TX (US)

(*) Notice: Subject to any disclaimer, the term of this patent is extended or adjusted under 35 U.S.C. 154(b) by 0 days.

(21) Appl. No.: 09/463,572

(22) PCT Filed: Jul. 17, 1998

(86) PCT No.: PCT/US98/14595

§ 371 (c)(1),
(2), (4) Date: Jan. 26, 2000

(87) PCT Pub. No.: WO99/06070

PCT Pub. Date: Feb. 11, 1999

Related U.S. Application Data

(60) Provisional application No. 60/054,307, filed on Jul. 29, 1997.

(51) Int. Cl.$^7$ .......................... A61K 31/715; C07H 1/00
(52) U.S. Cl. .......................... 514/912; 514/944; 514/54; 514/236.2; 536/123.1; 536/124; 536/128
(58) Field of Search ................... 514/912, 944, 514/54, 236.2; 536/123.1, 124, 128

(56) References Cited

U.S. PATENT DOCUMENTS

| | | | |
|---|---|---|---|
| 4,136,177 A | 1/1979 | Lin et al. | 424/211 |
| 4,136,178 A | 1/1979 | Lin et al. | 424/211 |
| 4,436,730 A | 3/1984 | Ellis et al. | 424/180 |
| 4,861,760 A | 8/1989 | Mazuel et al. | 514/54 |
| 5,082,579 A | 1/1992 | Dawson | 252/8.551 |
| 5,160,643 A | 11/1992 | Dawson | 252/8.551 |
| 5,273,056 A | 12/1993 | McLaughlin et al. | 128/898 |
| 5,607,698 A | 3/1997 | Martin et al. | 424/613 |
| 5,792,103 A | 8/1998 | Schwartz et al. | |
| 6,316,506 B2 * | 11/2001 | Asgharian | 514/839 |

FOREIGN PATENT DOCUMENTS

| | | |
|---|---|---|
| DE | 40 26 153 A | 2/1992 |
| WO | WO 93/25187 | 12/1993 |
| WO | WO 97/04012 | 2/1997 |
| WO | WO 97/30092 | 8/1997 |
| WO | WO 99/06070 | 2/1999 |

* cited by examiner

Primary Examiner—Samuel Barts
Assistant Examiner—Devesh Khare
(74) Attorney, Agent, or Firm—Barry L. Copeland

(57) ABSTRACT

The present invention is directed to viscoelastic systems comprising a combination of a galactomannan polysaccharide containing composition and borate containing composition. The two compositions gel or partially gel upon combination. The present invention also discloses methods of using the systems during surgery and, in particular, eye surgery.

10 Claims, 3 Drawing Sheets

METHODS OF PERFORMING SURGERY WITH GALACTOMANNAN POLYMERS AND BORATE

This application claims the benefit of Provisional Application No. 60/054,307, filed Jul. 07, 1999.

BACKGROUND OF THE INVENTION

The present invention relates to viscoelastic systems and methods of use. In particular, the present invention relates to switchable viscoelastic systems comprising compositions containing galactomannan polymers and borates. In general, the switchable viscoelastic systems are administered as a Part I viscous liquid during surgery, followed by the addition of a Part II gel-activating composition to the in situ Part I composition. The activation of the system provides a gel, allowing for the easy and complete removal of the viscoelastic system by aspiration.

Viscoelastic systems or materials generally comprise a polymer or mixture of polymers which exhibit both a viscous (adhesive) character and an elastic (cohesive) character. These compositions are useful for surgery because they provide some level of coatability to the tissues to be protected, and also are somewhat cohesive, allowing for aspiration of the composition following the termination of surgery. Viscoelastic compositions are useful in a number of different surgeries and, in particular, ocular surgeries.

Cataracts are opacities of the ocular lens which generally arise in the elderly. In order to improve eyesight, the cataractous lens is removed and an intraocular lens ("IOL") is inserted into the capsular bag. In order to maximize the procedure and post-surgical recovery, viscoelastic materials are injected in the anterior chamber and capsular bag to prevent collapse of the anterior chamber and to protect tissue from damage resulting from physical manipulation.

Trabeculectomy, i.e., glaucoma filtration surgery, involves the surgical creation of a fistula with a conjunctival flap which allows the direct drainage of aqueous humor from the anterior chamber into the conjunctival tissue. This procedure is used as an alternative to drug therapy, and allows for an increase in outflow of aqueous humor, thereby lowering the elevated intraocular pressure associated with glaucoma. In order to maintain a deep chamber and enhance visualization during the surgery, viscoelastic systems have been injected into the anterior chamber of the eye. The viscoelastic material used for such procedure may be difficult to aspirate out of the chamber following surgery. Ineffective or delayed removal of "lost" viscoelastic material in the anterior chamber can clog the natural drainage pores of the trabecular meshwork and actually lead to increased intraocular pressure. Thus, a need exists for the provision of improved viscoelastic compositions which are easily aspirated following filtration bleb surgery.

Vitrectomy surgery can also induce a variety of post-surgical complications. Many of these complications are further potentiated in diabetic patients who are at risk for many ocular pathologies. Due to the severity of the surgical procedure, the posterior segment surgery process can cause extensive tissue damage at both the acute and chronic phases of the recovery. The chronic phase of the postsurgical period is characterized by more severe complications that can necessitate additional surgery. These include an incidence of recurrent retinal detachment, epiretinal proliferation, neovascular glaucoma, corneal problems, vitreous hemorrhage, cystoid macular edema, and occurrence of cataract formation within six months of surgery. While various surgical irrigating and viscoelastic compositions are employed, the frequency of above-described complications still needs to be lessened by facilitating the recovery of vascular leakage and limiting the duration of the cellular proliferative response. Therefore, a need exists to improve the current effectiveness of viscoelastic compositions used in vitrectomy surgery.

Various viscoelastic compositions are available for surgical use. These compositions have employed various viscoelastic agents, such as sodium hyaluronate, chondroitin sulfate, polyacrylamide, HPMC, proteoglycans, collagen, methylcellulose, carboxymethyl cellulose, ethylcellulose, polyvinylpyrrolidone and keratan, all of various molecular weights and concentrations, and/or combinations thereof.

Those skilled in the art have formulated compositions containing the various viscoelastic agents described above to suit their particular needs. The suitability of a given agent has depended on the various function(s) which the agent is expected to perform and the surgical technique being employed by the surgeon. For example, for portions of surgical procedures involving phacoemulsification and tissue manipulation, e.g., cataract surgery, it has been generally preferable to use a viscoelastic agent that possesses relatively greater tissue coatability ("adherent" or "adhesive") properties and, consequently, relatively lesser cohesive properties. Those portions of surgical procedures involving manipulation of an IOL are generally better served by viscoelastic agents that possess relatively greater cohesive properties and relatively lesser adherent properties to maintain space. Such agents are referred to herein as "cohesive" agents.

Various viscoelastic agents have been employed in an effort to provide the above-described needs. For example, 5% HPMC provides good coatability for tissue protection. However, since tissue adhesion of this polymer is high, HPMC is more difficult to remove from the tissue, and such efforts of removal may adversely affect the tissue. This is also particularly critical in ocular surgery, as a residue of viscoelastic agent remaining in the eye following surgery can block the natural flow of aqueous humor and possibly induce glaucoma. On the other hand, polymers with a high degree of elasticity (cohesiveness) have provided ease and complete removal of the viscoelastic agent. However, these highly cohesive agents do not provide the proper level of coatability and hence, only provide a limited level of tissue protection. Thus, in most cases, it is desired to employ agents which possess extremes of both properties.

Since adhesion and cohesion properties are inversely related (i.e., increasing one property decreases the other), current viscoelastic agents do not possess a high degree of both properties, but in general, tend to exhibit a far greater magnitude of one property and considerably less character of the other property, or compromise between the two properties. In order to exploit the advantages of both types of properties, practitioners have employed viscoelastic regimens which employ two different compositions containing the different types of agents (see, e.g., U.S. Pat. No. 5,273,056 (McLaughlin et al.)).

SUMMARY OF THE INVENTION

The present invention is directed to switchable viscoelastic systems. The viscoelastic systems of the present invention comprise a two-part gelable system, wherein the gel is created by the variable crosslinking of a borate compound with one or more galactomannans. The gelation is completely reversible by manipulating pH.

In use, a Part I composition, containing one or more galactomannans in the presence or absence of a borate compound, is administered during surgery as an adherent composition. When the next phase of surgery is to be initiated, the Part II composition, comprising a crosslinking amount of a borate compound, is administered to the in situ Part I composition, thereby activating or further activating the gelation of the galactomannan containing composition. The admixture of Part I and II forms a highly cohesive composition which provides space maintenance capabilities and easy aspiration of the viscoelastic system at the close of surgery.

The viscoelastic systems of the present invention provide the advantages of a switchable gelling system, wherein a composition may be administered as a liquid or partially gelled liquid and later converted to a gel. Accordingly, one advantage of the viscoelastic systems of the present invention is that they provide optimal levels of both adhesive properties and cohesive properties in a single system. Another advantage of the systems is that they are switchable, i.e., they may be converted from an adherent system to a cohesive system during surgery. Current viscoelastic compositions have employed hyaluronic acid and other naturally occuring polymers. The preparation and sterilization of these agents is generally expensive, resulting in relatively expensive viscoelastic compositions. The systems of the present invention comprise relatively inexpensive agents. Thus, another advantage of the systems of the present invention is that they are relatively low in cost to produce. Still another advantage of the systems of the present invention is that they provide a relatively high degree of reproducibility of the gel charcteristics through various types and sources of galactomannan (see, FIG. 3). This feature allows for the interchange of sourcing without extensive reworking of the compositions of the present invention.

The methods of the present invention involve the surgical use of the compositions of the present invention.

The present invention is also directed to methods of sterilization of the galactomannans involving autoclaving.

DETAILED DESCRIPTION OF THE INVENTION

Figure 1:
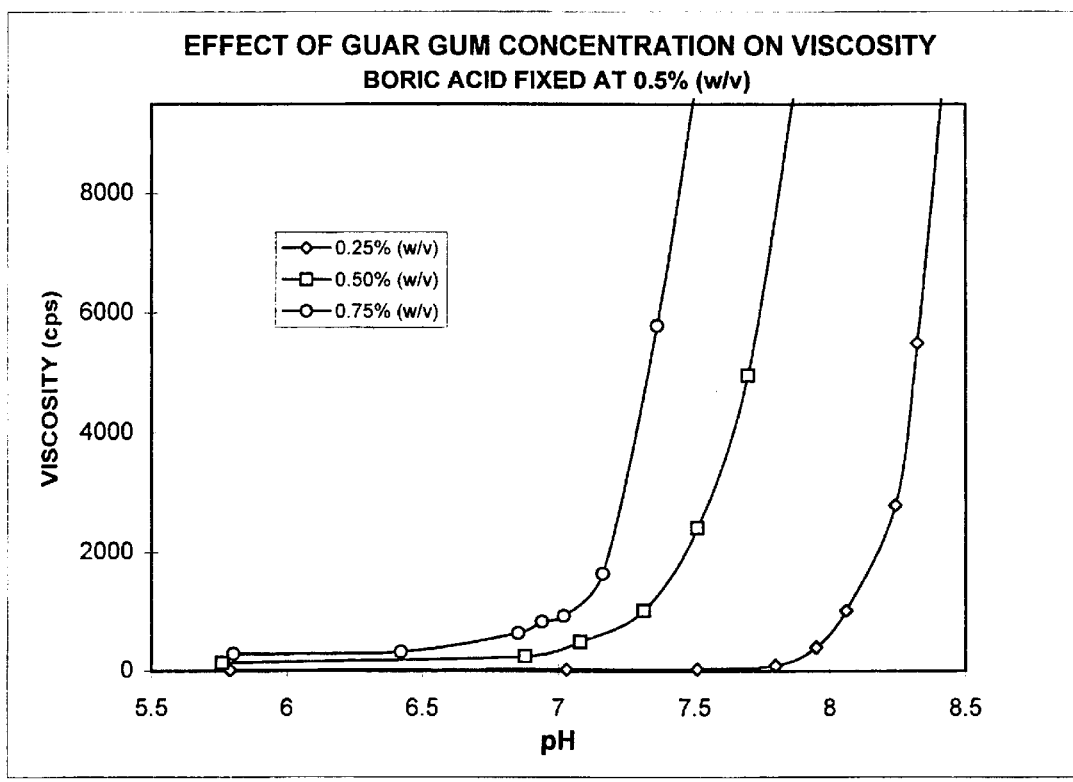
FIG. 1 is a graph illustrating the gelling characteristics of various concentrations of guar gum in the presence of borate, relative to pH.

The present invention is directed to viscoelastic systems which comprise compositions containing one or more galactomannan polysaccharide(s) and one or more borate compound(s). The present invention is also directed to methods of using these compositions to treat various surgeries and, in particular, ophthalmic surgeries such as cataract, trabeculectomy and vitrectomy surgeries.

The compositions of the present invention comprise a two-part system. The two compositions are formulated in such a way that an increase or decrease of the gelation of the first part is manipulated by the admixture of the second part with the first part. Accordingly, the first part, referred to herein as "Part I," will comprise one or more galactomannan polymer(s) and optionally an amount of a borate compound. In general, the second part, referred to herein as "Part II," will comprise a crosslinking amount of at least one borate compound. As used herein, the term "crosslinking amount" refers to that amount of a borate compound sufficient to facilitate the borate-galactomannan crosslinking of the Part I and Part II compositions, such that the admixture of the compositions increases in viscosity and cohesiveness over the Part I composition. Alternatively, the Part I composition may contain both the galactomannan and borate compounds at a slightly acidic pH relative to physiological pH, and the Part II composition may contain a saline solution capable of increasing the pH of the Part I composition, such that gelation is accomplished by the admixture of Parts I and II.

Is The types of galactomannan that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1−4)-β-D-mannopyranosyl units with α-D-galactopyranosyl units attached by (1−6) linkages. With the preferred galactomannans, the ratio of D-galactose to D-mannose will vary, but generally will be from about 1:2 to 1:4. Galactomannans having a D-galactose:D-mannose ratio of about 1:2 are most preferred.

In order to limit the extent of cross-linking and provide a softer gel characteristic, chemically modified galactomannans may be utilized. Accordingly, chemically modified variations of the polysaccharides described above are also included in the "galactomannan" definition. For example, hydroxyethyl, hydroxypropyl and carboxymethylhydroxypropyl substitutions may be made to the galactomannans of the present invention. If it is desired to modify the galactomannans, non-ionic substitutions of the galactomannans, such as those containing alkoxy and alkyl (C1–C6) groups are particularly preferred (e.g., hydroxylpropyl substitutions). Substitutions in the non-cis hydroxyl positions are most preferred. An example of non-ionic substitution of a galactomannan of the present invention is hydroxypropyl guar. with a molar substitution ratio of less than about 0.6.

The borate compounds which may be used in the compositions of the present invention are boric acid and other pharmaceutically acceptable salts such as sodium borate (borax) and potassium borate. As used herein, the term "borate" refers to all pharmaceutically suitable forms of borates.

The Part I compositions of the viscoelastic systems of the present invention comprise one or more galactomannan(s) in an amount of from about 0.5 to 5.0% weight/volume ("w/v"). Preferably, the compositions will contain 1.0 to 3.0% (w/v) of galactomannan, and most preferably, the compositions will contain 1.0 to 2.0% (w/v) of galactomannan. As stated above, the Part I composition may optionally contain a borate compound. If a viscosity greater than that of a non-crosslinked galactomannan Part I composition is desired. than a variable crosslinking amount of a borate compound may be added to the composition to facilitate a minor to partially gelled nature (and greater viscosity) of the Part I composition. Such an amount of a borate compound will depend on the amount of galactomannan present, the tonicity and pH levels of the Part I composition, as well as the presence of other ingredients. In general, such an amount of borate will be up to 5.0% (w/v).

The Part II compositions of the viscoelastic systems of the present invention will generally comprise a crosslinking amount of a borate compound. In general, such an amount will be from about 0.05 to 5% (w/v). Preferably, the compositions will contain 0.05 to 2.0% (w/v) of a borate compound, and most preferably, the compositions will contain 0.1 to 0.75% (w/v) of a borate compound. Alternatively, the Part I composition will comprise all of the borate compound, wherein the Part II composition will comprise an amount of tonicity and pH affecting agent(s) necessary to facilitate gelation of the admixture of Part I and Part II.

Figure 2:
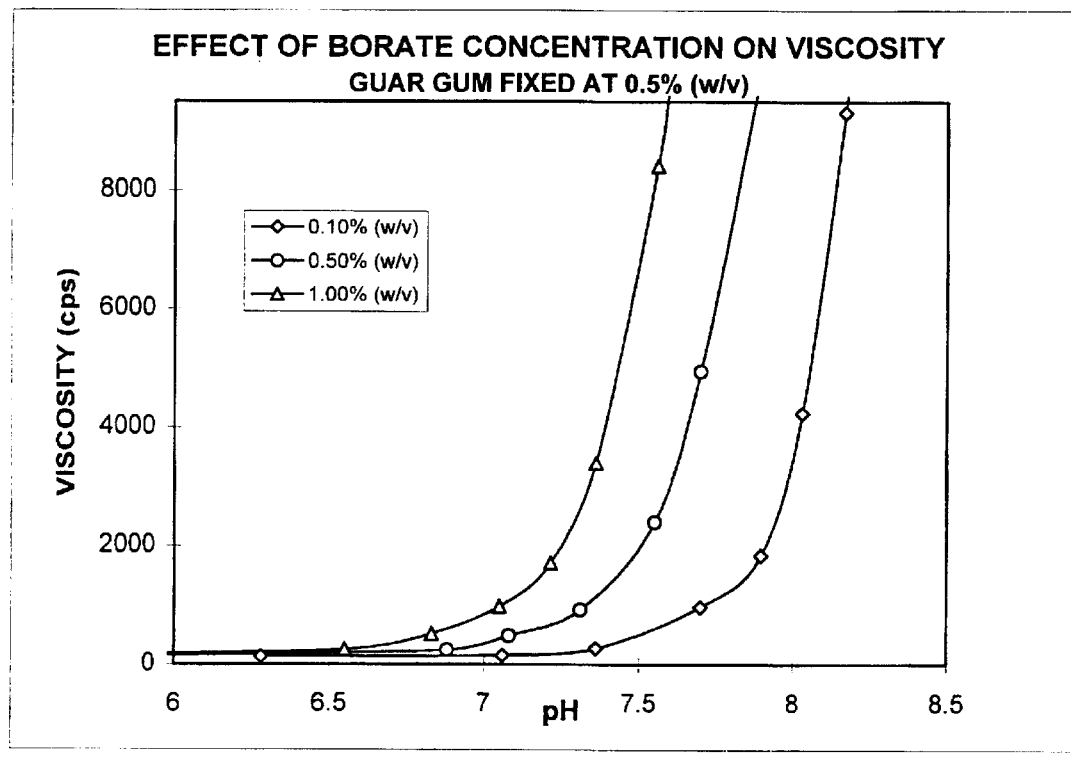
FIG. 2 is a graph illustrating the gelling characteristics of various concentrations of borate in the presence of guar gum, relative to pH.
Figure 3:
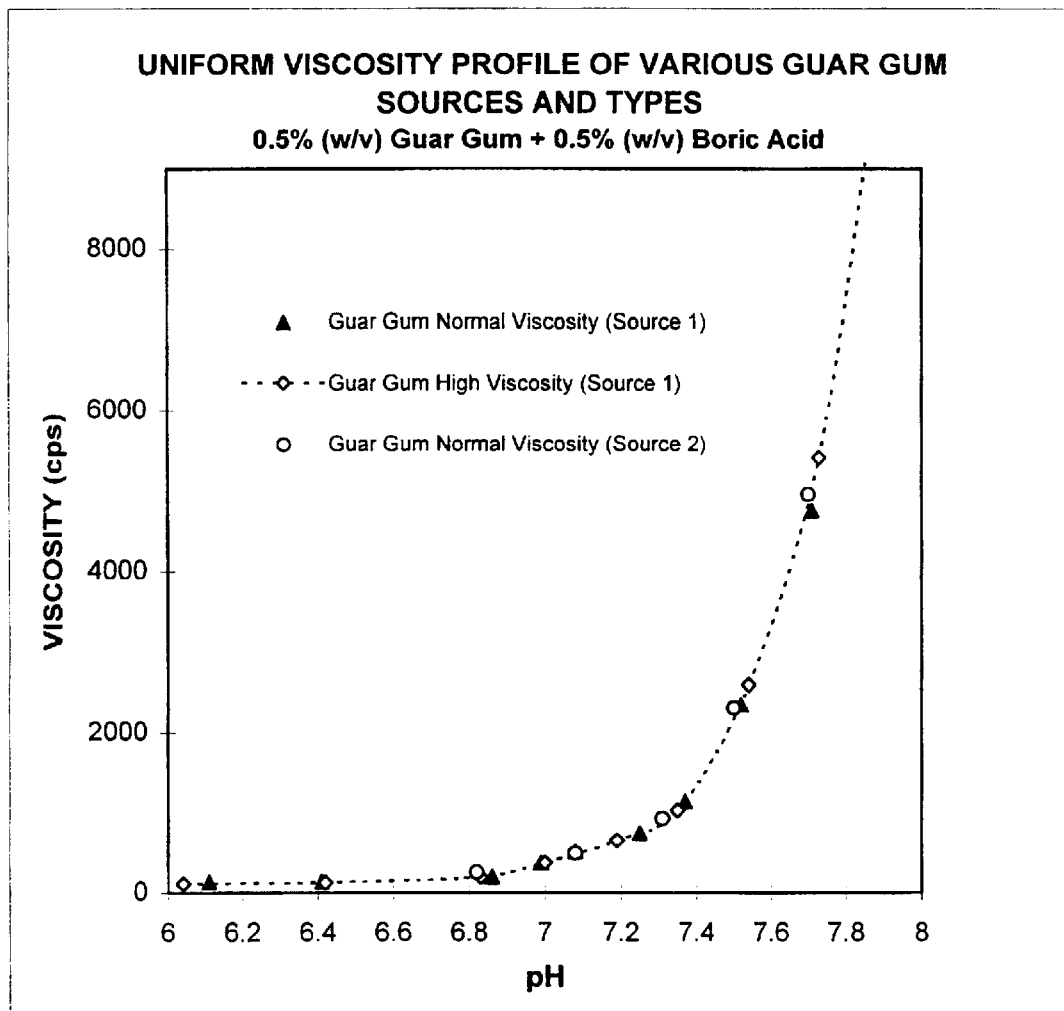
FIG. 3 is a graph illustrating the uniformity of the gelling characteristics of three different types/sources of guar gum.

The particular amounts of the galactomannan and borate will vary, depending on the particular gelling properties desired. In general, the borate or galactomannan concentration may be manipulated in order to arrive at the appropriate viscosity of the Part I composition, and the appropriate viscosity/cohesiveness of the combination of the Part I and Part II compositions. As shown in FIGS. 1 and 2, manipulating either the borate or galactomannan concentration provides stronger or weaker gelation at a given pH. If a strongly gelling composition is desired, then the borate or galactomannan concentration may be increased. If a weaker gelling composition is desired, such as a partially gelling composition, then the borate or galactomannan concentration may be reduced. Other factors may influence the gelling features of the compositions of the present invention, such as the nature and concentration of additional ingredients in the compositions, such as salts, pharmaceutically active agents, and so on. Generally, preferred non-gelled Part I compositions of the present invention, i.e., compositions exhibiting a relatively high adhesive character, will have a viscosity of from about 500 to 50,000 cps.

The galactomannans of the present invention may be obtained from numerous sources. Such sources include guar gum, locust bean gum and tara gum, as further described below. Additionally, the galactomannans may also be obtained by classical synthetic routes or may be obtained by chemical modification of naturally occurring galactomannans.

Guar gum is the ground endosperm of *Cyamopisis tetragonolobus (L.) Taub.* The water soluble fraction (85%) is called "guaran"(molecular weight of 220,000), which consists of linear chains of (1–4)-β-D mannopyranosyl units with α-D-galactopyranosyl units attached by (1–6) linkages. The ratio of D-galactose to D-mannose in guaran is about 1:2. The gum has been cultivated in Asia for centuries and is primarily used in food and personal care products for its thickening property. It has five to eight times the thickening power of starch. Its derivatives, such as those containing hydroxypropyl or hydroxypropyltrimonium chloride substitutions, have been commercially available for over a decade. Guar gum can be obtained, for example, from Rhone-Polulenc (Cranbury, N.J.). Hercules. Inc. (Wilmington, Del.) and TIC Gum, Inc. (Belcamp, Md.).

Locust bean gum or carob bean gum is the refined endosperm of the seed of the carob tree, *ceratonia siliqua*. The ratio of galactose to mannose for this type of gum is about 1:4. Cultivation of the carob tree is old and well known in the art. This type of gum is commercially available and may be obtained from TIC Gum, Inc. (Bekamp, Md.) and Rhone-Polulenc (Cranbury, N.J.).

Tara gum is derived from the refined seed gum of the tara tree. The ratio of galactose to mannose is about 1:3. Tara gum is not produced in the U.S. commercially, but the gum may be obtained from various foreign sources.

Substituted galactomannans are commercially available from Rhone-Poulenc (Cranbury, N.J.).

Other ingredients may be added to the Part I compositions of the present invention. Such ingredients generally may include tonicity adjusting agents, active pharmaceutical agent(s) and pH adjusting agents. If relatively insoluble pharmaceutical agent(s) are to be added to the Part I compositions, then various solubilizers may be employed to aid in the solubilization of the agent(s). Other polymer or monomeric agents such as polyethylene glycol and glycerol may also be added for special processing. Tonicity agents useful in the compositions of the present invention may include salts such as sodium chloride, potassium chloride and calcium chloride; non-ionic tonicity agents may include propylene glycol and glycerol; solubilizing agents may include Cremophor EL® and tween 80; and pH adjusting agents may include hydrochloric acid, Tris, triethanolamine and sodium hydroxide. In general, the Part I compositions will be packaged for unit dose application. With these types of packagings, the product is sterile packaged and used for one surgical procedure, with any remaining product discarded. If, however, the Part I compositions of the present invention are packaged for multi-dose application, a suitable preservative will be added to the composition. Suitable preservatives may include, for example, benzalkonium chloride, polyquaternium-1 and polyhexamethylene biguanide. The above listing of examples is given for illustrative purposes and is not intended to be exhaustive. Examples of other agents useful for the foregoing purposes are well known in the field of ophthalmic formulation and are contemplated by the present invention.

Other agents may be added to the Part II compositions of the present invention. Such ingredients include those generally described in the preceding paragraph. The primary function of Part I compositions, however, is to activate a gel in combination with the Part I composition. Thus, while the Part I composition is added to the tissue situs for therapeutic purposes, the Part II composition is generally only utilized to prepare a cohesive and hence, easily aspiratable and quickly removable gel combination of Part I and Part II. Therefore, the Part II compositions generally will only comprise other ingredients necessary to transfer the crosslinking amount of a borate compound to the Part I composition. Such ingredients typically will be salts or other tonicity agents, and water. As stated above, if the Part I composition optionally contains both the galactomannan and borate compound at a slightly acidic pH, then the Part II composition may be formulated to deliver an amount of tonicity agent/pH modifying agent to facilitate gel formation. In general, similar to the Part I compositions, the Part II compositions will typically be formulated for unit dose application. If, however, the Part II compositions of the present invention are packaged for multi-dose application, a suitable preservative will be added to the composition. Suitable preservatives may include those described above.

Sterilization of the galactomannan polysaccharide can be accomplished by autoclaving. Since the polymers undergo depolymerization at the extreme conditions of autoclaving, non-aqueous autoclaving is generally preferred. This can be accomplished by dispersing the polymer in a suitable organic liquid such as low molecular weight polyethylene glycols. The resulting suspension may then be autoclaved to sterilize the polymer. The sterilized polymer is then hydrated aseptically, prior to admixture with the other ingredients. The following example illustrates a novel method of sterilizing a galactomannan polysaccharide of the present invention:

EXAMPLE 1

Preliminarily, a compounding vessel (20 L stainless steel pressure can), a 0.2 micron sterilizing filter, a receiving vessel (20 L carboy), a 4.5 micron polishing filter, a 0.2 micron sterilizing filter, a vent filter, and the filling equipment are sterilized by autoclaving.

In a beaker equipped with an overhead agitator, add the weighed amount of polyethylene glycol 400 (200 g). While mixing slowly disperse the weighed amount of hydroxypropyl ("HP")Guar gum (100 g). Mix until completely homogeneous. In a 500 ml Schott bottle, equipped with a magnetic stir bar, weigh exactly 120.0 g of the HPGuar gum/PEG-400 dispersion. Prepare to sterilize by autoclaving. In a second identical 500 ml Schott bottle weigh exactly 120.0 g of the same dispersion. Prepare to use as a dummy during the autoclaving cycle. To both bottles add 1.3 ml of purified water (amount equivalent, by volume, of the microorganism suspension used to inoculate the bottles during the validation study). Mix both bottles for 10 minutes using a magnetic stir plate. Autoclave the HPGuar gum/PEG-400 dispersion using the validated time-temperature cycle of 80 minutes at 125° C.

The other set of ingredients to be included in the final formulation may be prepared separately by various methods known in the art. The resultant mixture can be added by sterile filtration to the compounding vessel, along with the HPGuar gum/PEG-400 preparation.

Aseptically transfer the sterilized HPGuar gum/PEG-400 dispersion into the pre-sterilized compounding vessel. Rinse the bottle content with sterilized purified water. Bring the content of the compounding vessel to exactly 95% of the theoretical batch weight (19.0 liters or 19.06 Kg) using sterile room temperature purified water. Allow the HPGuar gum/PEG slurry to hydrate while mixing, at moderate speed, in the compounding vessel for a minimum of 2 hours. Transfer the contents of the compounding vessel through a 4.5 micron pre-sterilized polishing filter into the pre-sterilized receiving vessel equipped with a stir bar. There will be some loss of the contents due to the product held in filter housing and filter cartridge. (If a pressure can is used as compounding vessel, the recommended pressure for clarification filtration is approximately 30 psi.) Check and adjust pH, if necessary, to 6.9–7.1 (target 7.0) using 1N NaOH or 1N HCl. Approximately 3–4 ml of 1N NaOH per 1 liter of final batch weight is needed to achieve the desired pH. QS to final batch weight using sterile purified water. Mix at low speed for a minimum of 30 minutes.

The methods of the present invention involve the use of various viscoelastic agents having different adherent or cohesive properties. Those skilled in the art will recognize that the systems of the present invention may be employed by the skilled surgeon in a variety of surgical procedures.

For portions of surgical procedures involving phacoemulsification and/or tissue manipulation, e.g., cataract surgery, Part I viscoelastic compositions that possess relatively greater adherent properties and relatively lesser cohesive properties will provide superior tissue protection. For Part I compositions such as these, which are being employed primarily for protective purposes, a functionally desirable viscosity will be a viscosity sufficient to permit a protective layer of such agent to remain on the tissue or cells of concern during the surgical step(s) being performed. Such viscosity will typically be from about 500 cps to about 50,000 cps (at shear rate of 2 $sec^{-1}$ and 25° C.), and preferably will be about 10,000 to about 40,000 cps. Such adherent agents are capable of providing the protective function previously discussed, yet are not prone to inadvertent removal, which could jeopardize the delicate tissue being protected. The Part I adherent compositions of the present invention may also be used for space maintainance purposes prior to application of Part II compositions.

Following the phacoemulsification step, those portions of surgical procedures involving intraocular lens manipulation are generally better served by gel-activated viscoelastic systems (Part I and Part II compositions) that provide space filling requirements and ease of removal. Such agents are referred to herein as "cohesive" agents. For highly cohesive gel-activated systems (i.e., combined Part I and Part II compositions) which are being employed primarily for space maintainance purposes as opposed to protective purposes, a functionally desirable viscosity will be a viscosity sufficient to permit the skilled surgeon to use such agent as a soft tool to manipulate or support the tissue of concern during the surgical step(s) being performed. Such highly cohesive agents are capable of maintaining intraocular space and manipulating tissue without adhering to it. When their purpose has been served, they can, because of their cohesive properties, be readily removed with minimal trauma to the surrounding tissue. Furthermore, when a Part I composition of the present invention is gel activated by the addition of a Part II composition of the present invention, the gel (having greater cohesive property) may be easily and completely removed. thereby minimizing complications resulting from excessive aspirating of the less cohesive agents and the possible intraocular pressure spike resulting from the incomplete removal of the adherent compositions in situ.

The present invention may also be used in corneal transplant surgery. In conjunction with the removal of the patient's corneal button, it is desirable to replace the aqueous humor with a highly viscous agent that will provide a firm bed to support the donor cornea, yet be susceptible to easy removal upon completion of the surgery. The donor graft, on the other hand, requires maximum protection from the surgical trauma and should therefore be coated with a different, more adherent agent. Corneal transplant surgery also involves the risks of inflammation and cellular damage. Thus, the compositions of present invention are also useful in this type surgery.

The compositions of the present invention may also be used in posterior segment surgery. In a retinal detachment procedure, for example, a highly viscous, cohesive composition of the present invention will be used to manipulate the retina into position against the basement membrane of the choroid. Small amounts of a more adherent composition of the present invention may be injected behind the retina before or after such manipulation to temporarily maintain the contact between the retina and basement membrane while more permanent attachment procedures well known to those skilled in the art are performed (e.g. tacking or laser welding).

The methods of the present invention are also directed to using the systems of the present invention to ameliorate complications arising from glaucoma filtration surgery. Glaucoma filtration surgery involves the surgical creation of a fistula with a conjunctival flap which allows the direct drainage of aqueous humor from the anterior chamber into the conjunctival tissue thereby lowering the elevated intraocular pressure associated with glaucoma. However, in many patients, the filtration "bleb" becomes scarred or healed over so that aqueous drainage can no longer occur. In order to maintain a deep chamber and enhance visualization during the surgery, the viscoelastic systems of the present invention will be injected into the anterior chamber of the eye. The addition of these systems will ameliorate inflammatory conditions resulting from the surgery, fibroplasia and decrease bleb failure.

The following examples further illustrate preferred ophthalmic viscoelastic compositions of the present invention:

EXAMPLE 2

The following is an example of a viscoelastic system comprising a Part I viscoelastic composition and Part II gel-activation composition:

Part I:

| Compound | Amount % (w/v) |
| --- | --- |
| Guar Gum | 2.0 |
| Polyethylene Glycol 400 ("PEG-400") | 2.0 |
| Sodium Chloride | 0.6 |
| Sodium Hydroxide/Hydrochloric Acid | pH 7.4 |
| Purified Water | QS |

The above formulation is prepared by first dispersing guar gum in PEG-400, and autoclaving the suspension (Part I). Sodium chloride is then dissolved in 50% of the volume of water and sterile filtered in a receiving vessel as Part II. Part I is then added to Part II aseptically and the polymer is allowed to hydrate. The pH may then be adjusted aseptically and the batch is then brought to final weight (volume). The combined solution is then passed through a 1.0 μm polish filter, aseptically, to remove the particulates.

Part II:

| Compound | Amount % (w/v) |
| --- | --- |
| Sodium Borate | 0.25 |
| Sodium Chloride | 0.4 |
| Sodium Hydroxide/Hydrochloric Acid | pH 7.4 |
| Purified Water | QS |

The invention in its broader aspects is not limited to the specific details shown and described above. Departures may be made from such details within the scope of the accompanying claims without departing from the principals of the invention and without sacrificing its advantages.

What is claimed is:

1. A method of performing surgery on an eye, which comprises:

instilling into the eye a Part I viscous composition comprising one or more galactomannan; and adding to the Part I composition in the eye a Part II crosslinking composition comprising a crosslinking amount of one or more borate compound to form a cohesive, gelled combination of the Part I and Part II compositions having a greater viscosity and cohesivity than the viscosity and cohesivity of the Part I composition alone.

2. The method of claim 1, wherein the concentration of the galactomannan in the Part I composition is about 0.5 to 5.0% (w/v) and the concentration of the borate compound in the Part II composition is about 0.05 to 2.0% (w/v).

3. The method of claim 1, wherein the galactomannan is selected from the group consisting of guar gum, locust bean gum, tara gum and chemically modified derivatives thereof.

4. The method of claim 1, wherein the borate compound is selected from the group consisting of boric acid, sodium borate, potassium borate and combinations thereof.

5. The method of claim 1, wherein the galactomannan is hydroxypropyl guar and the borate compound is boric acid.

6. The method of claim 5, wherein the hydroxypropyl guar is in a concentration of 1.0 to 3.0% (w/v) and boric acid is in a concentration of 0.1 to 0.75% (w/v).

7. The method of claim 1, wherein the galactomannan is guar gum and the borate compound is boric acid.

8. The method of claim 7, wherein the Part I composition comprises guar gum in a concentration of 1.0 to 3.0% (w/v) and the Part II composition comprises boric acid in a concentration of 0.1 to 0.75% (w/v).

9. The method of claim 1, wherein the Part I composition further comprises one or more pharmaceutically active agent (s).

10. The method of claim 9, wherein the pharmaceutically active agent is selected from the group consisting of: anti-hypertensive, anti-glaucoma, neuro-protective, angiostatic, anti-microbial, and anti-inflammatory agents.

* * * * *